US008310544B2

(12) United States Patent
Kim et al.

(10) Patent No.: US 8,310,544 B2
(45) Date of Patent: Nov. 13, 2012

(54) HAND-HELD INSPECTION TOOL AND METHOD

(75) Inventors: Moon S. Kim, Silver Spring, MD (US);
Alan M. Lefcourt, Elkridge, MD (US);
Kuanglin Chao, Ellicott, MD (US);
Yud-Ren Chen, Laurel, MD (US);
Andre G. Senecal, North Smithfield, RI (US); Patrick Marek, Shrewsbury, MA (US)

(73) Assignees: The United States of America as represented by the Secretary of Agriculture, Washington, DC (US); The United States of America as represented by the Secretary of the Army, Washington, DC (US)

( * ) Notice: Subject to any disclaimer, the term of this patent is extended or adjusted under 35 U.S.C. 154(b) by 1042 days.

(21) Appl. No.: 12/157,911

(22) Filed: Jun. 13, 2008

(65) Prior Publication Data

US 2009/0309967 A1 Dec. 17, 2009

(51) Int. Cl.
*H04N 7/18* (2006.01)
(52) U.S. Cl. .......................... 348/143; 348/89
(58) Field of Classification Search .................. 348/143, 348/89, 127
See application file for complete search history.

(56) References Cited

U.S. PATENT DOCUMENTS

| 5,305,356 | A | * | 4/1994 | Brooks et al. | 376/249 |
| 5,505,090 | A | * | 4/1996 | Webster | 73/657 |
| 5,838,840 | A | * | 11/1998 | King et al. | 382/300 |
| 7,110,586 | B2 | * | 9/2006 | Bacus et al. | 382/128 |
| 2003/0064025 | A1 | * | 4/2003 | Yang et al. | 424/9.6 |
| 2004/0001333 | A1 | * | 1/2004 | Gentz | 362/103 |
| 2004/0109059 | A1 | * | 6/2004 | Kawakita | 348/143 |
| 2009/0261966 | A1 | * | 10/2009 | Cutchis | 340/522 |

OTHER PUBLICATIONS

VerifEYE Technologies (corportation), Presentation dated Mar. 2003, published on the company web site at www.verifeye.com.
Comis, Don, Machine's Eye View of Poultry and Produce, Agriculture Research Magazine, Jan. 18-19, 2007.

* cited by examiner

*Primary Examiner* — David Lazaro
*Assistant Examiner* — Marie Georges Henry
(74) *Attorney, Agent, or Firm* — John Fado; Robert D. Jones; Lesley Shaw (57) ABSTRACT

The hand-held inspection tool enhances the ability of an on-site inspector to detect and communicate the presence of contamination on an object or in an area. An on-site inspector directs an excitation light in the sensing head of the tool into an area of interest. If the targeted contamination is present, the excitation light causes the contamination to emit fluorescence. The emitted fluorescent light passes through a narrow spectral band-pass video camera filter and is detected by a video camera mounted in the tool sensing head. The video camera transmits the image to a display visible to the on-site inspector. The invention also includes a means of recording, documenting, and wirelessly communicating the inspection process so that remotely located personnel can view the inspection, and respond to the inspection findings in real time.

34 Claims, 12 Drawing Sheets

HAND-HELD INSPECTION TOOL AND METHOD

FIELD OF THE INVENTION

The present invention relates to an inspection tool and an associated method of inspection. Specifically, the invention relates to a specialized hand-held tool that incorporates a lighting device, a corresponding camera system, and a communication means. The tool enhances the ability of an on-site inspector to detect and communicate the presence of contamination on a targeted object or in a targeted area.

BACKGROUND OF THE INVENTION

Food contamination is a major concern for food processors, wholesale food suppliers, and restaurants that serve the public. Organisms such as *Escherichia coli, Salmonella,* and *Listeria* have been associated with multiple incidents of food related illnesses and some deaths.

Most current food inspection methods rely heavily on the ability of individual human inspectors to see, identify, and target for removal any contamination present. However, many types of contamination are not easily visible to the human eye in normal lighting conditions. Inspector fatigue, less than ideal inspection conditions, and production pressures may also impact the quality of food inspections. Further, it would be advantageous if multiple remotely located inspectors could simultaneously participate in an inspection and document the inspection process for later examination and verification.

To address these issues, some automated food inspection processes and facilities have been developed. However, these processes generally rely on relatively large fixed-base mechanisms that (for example) straddle a production conveyor. Although these automated inspection methods represent an advance over previous inspection processes, their expense, lack of mobility, and process integration requirements limit their utility.

The need exists for a relatively inexpensive mobile inspection device that gives an inspector the ability to conduct a thorough inspection and to document the inspection for later examination. The current invention allows an inspector the flexibility to direct a specialized contamination inspection tool up, over, under, and around a target item. The inspection tool also allows an inspector to view and record the target item under selected spectral conditions, and simultaneously transmit the image to other remotely located inspectors who may conduct complementary or overlapping inspections. The recording means allows the inspector to document the inspection process for later examination by potential customers, regulatory organizations, and others who have an interest in the inspection process. The current invention also allows the remote inspectors to conduct further analysis and send images back to the on-site inspector in real time for display of the analyzed image.

SUMMARY OF THE INVENTION

The current invention is directed to a hand-held inspection tool comprised of a sensing head connected to a generally rectangular body. The sensing head and the body of the tool are supported by an operator hand grip. A video camera is positioned in the tool so that the lens of the video camera is exposed on the tool sensing head. At least one narrow spectral band-pass video camera filter covers the video camera lens. The video camera filter is chosen so that only a selected wave band of light passes through the video camera filter to the camera lens.

The sensing head also includes at least one excitation light disposed on the face of the sensing head. The light induces a target to emit fluorescence corresponding with the selected wave band of light that passes through the video camera filter to the video camera lens. A visual display system displays the light detected by the camera so that the fluorescence emitted by the target is displayed, recorded, and wirelessly transmitted by the tool. A computer processing station receives the wirelessly transmitted information and makes the information available to remotely located inspectors on a real-time basis.

The current invention is also directed to a method of conducting an inspection. The method comprises providing a hand-held inspection tool body and attaching a sensing head to the tool body. A video camera is installed in the tool so that the lens of the video camera is exposed on a face of the sensing head. The lens of the video camera is covered with a spectral band-pass video camera filter so that only a selected wave band of light passes through the video camera filter to the video camera lens. At least one excitation light is positioned on the face of the sensing head. The light projects a light wavelength that induces target contamination to emit fluorescence corresponding with the selected wave band of light that passes through the video camera filter. An electronic processor in the tool to receives and transmits video images from the video camera. A display in communication with the tool receives video images from the video processor and allows an on-site inspector to view the video images transmitted from the processor.

In operation, the tool body and sensing head are supported by a hand grip attached to the tool body. An on-site inspector activates the light and directs the sensing head toward an area of interest so that any target contamination in the area of interest emits fluorescence. The fluorescence passes through the spectral band-pass camera filter and is recorded by the video camera. The fluorescent image is displayed on the display to alert the on-site inspector to the presence of the target contamination. The video camera images are also wirelessly transmitted by the tool. A computer processing station receives the wirelessly transmitted information and makes the information available to remotely located inspectors on a real-time basis. The remotely located inspectors may also communicate with the on-site inspector in real-time.

DETAILED DESCRIPTION OF PREFERRED EMBODIMENTS

Figure 1:
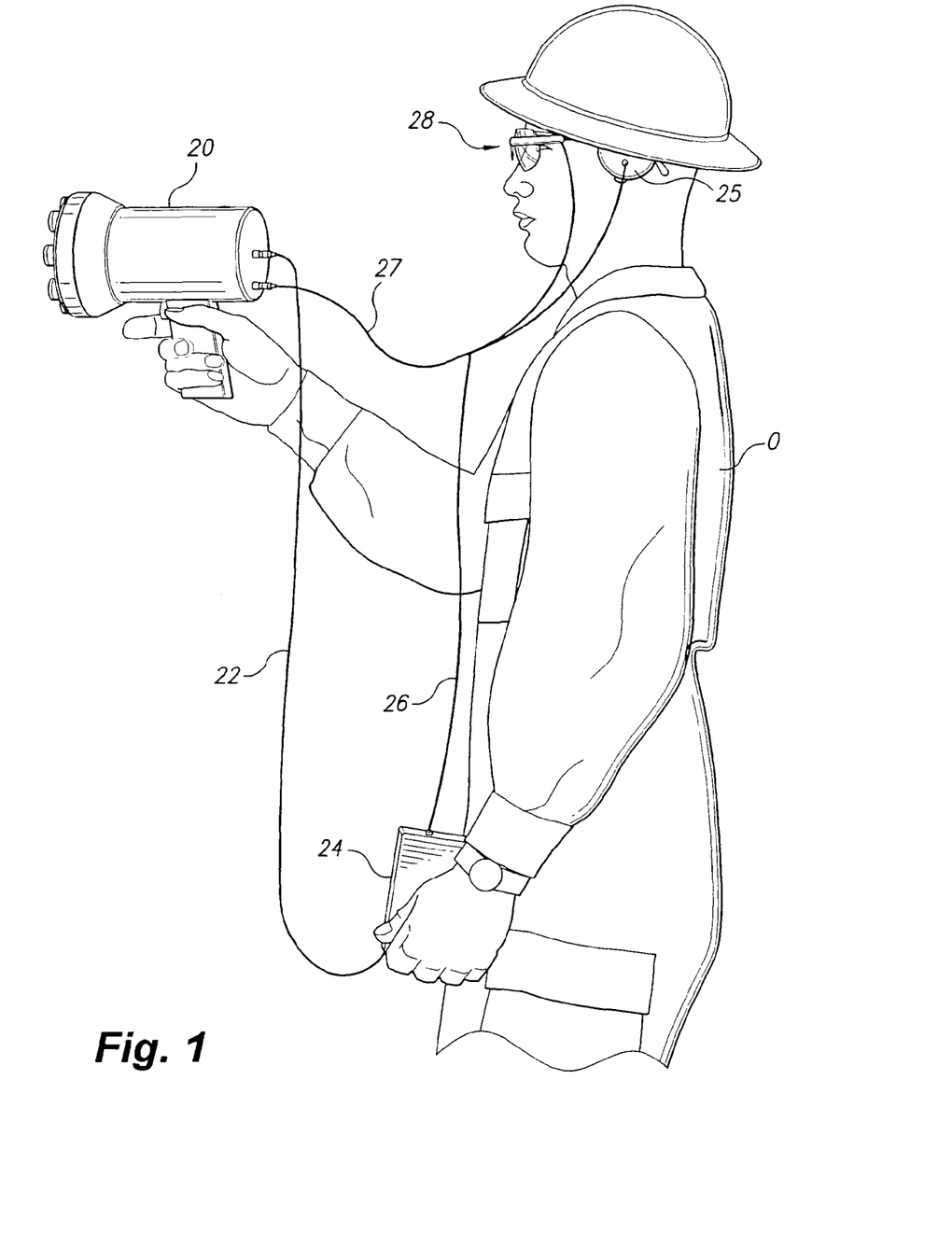
FIG. 1 is an environmental view of the preferred embodiment of the inspection system of the current invention.

The present invention comprises a hand-held inspection tool, as generally shown in FIG. 1. In the preferred embodiment, the hand-held inspection tool 20 is linked via cable 22 to an image processor 24, which is, in turn, linked via cable 26 to a monocle display system 28. During an inspection, an on-site inspector O uses the inspection tool 20 to collect images of a target inspection item or area, and transmits the images through the image processor 24 to the monocle display system 28 so that the on-site inspector O can supplement his traditional visual inspection with the enhanced images captured by the inspection tool 20. The tool 20 includes the capability of wirelessly transmitting the images to a computer processing station for further dissemination to remotely located inspectors and other personnel. Acquired images can be analyzed by the computer processing station and transmitted back to the hand-held inspection tool 20 for viewing.

The tool 20 also has an audio transmission and reception capability which allows two-way communication between the on-site inspector O and remotely located personnel. The audio transmissions received by the on-site inspector O are directed from the inspection tool 20 to a speaker system 25 via a transmission cable 27. In the preferred embodiment, the speaker system 25 comprises a set of headphones that are well-known in the art. However, the exact form of the speaker system 25 may include any audio device known in the art, including a simple stereo-type speaker mounted in or on the inspection tool 20. The communication aspects of the invention are discussed in greater detail infra.

Figure 2:
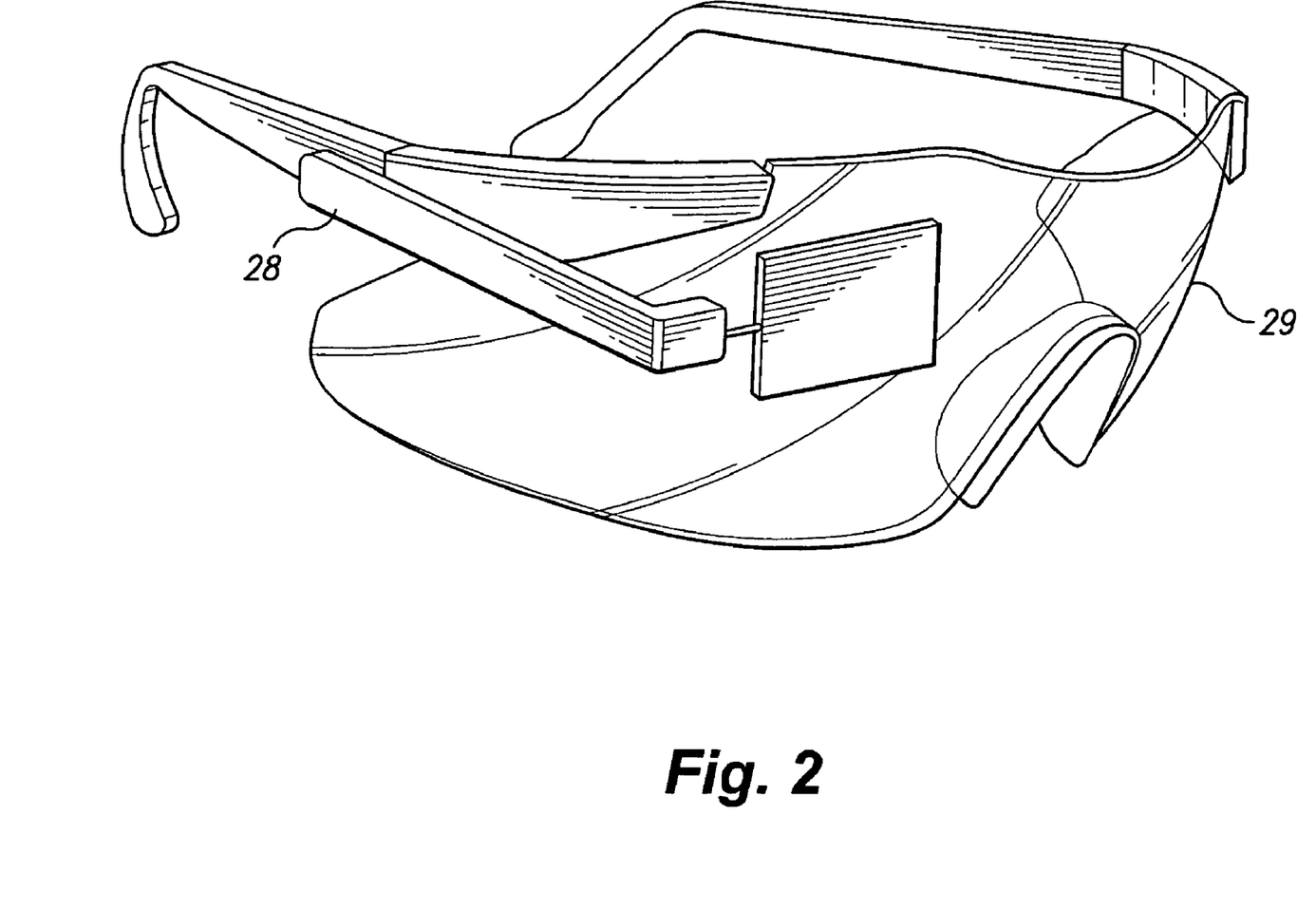
FIG. 2 is a front perspective view of the monocle display system.

As generally shown in FIG. 2, the monocle display system 28 may be mounted on safety goggles 29 so that an on-site inspector O only has to briefly divert his eyes to observe the enhanced images transmitted by the inspection tool 20. The specific configuration of the monocle display system 28 may include any system known in the art consistent with the functions as described above. In alternative embodiments, the image transmitted by the inspection tool 20 may be displayed by other means, including a larger display screen that is physically attached to the inspection tool 20 (see the embodiment shown in FIG. 11)

Figure 3:
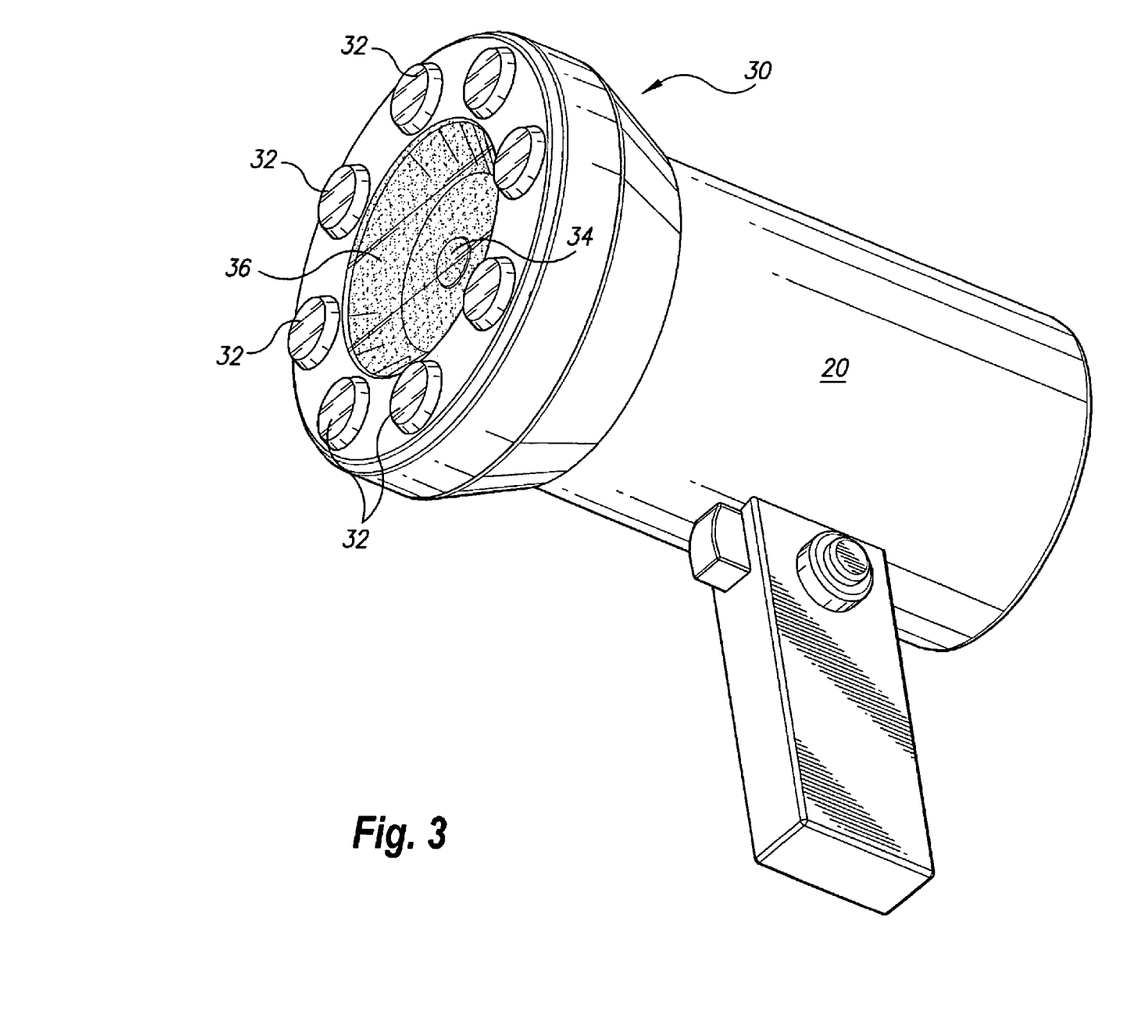
FIG. 3 is a perspective view of the basic embodiment.
Figure 4:
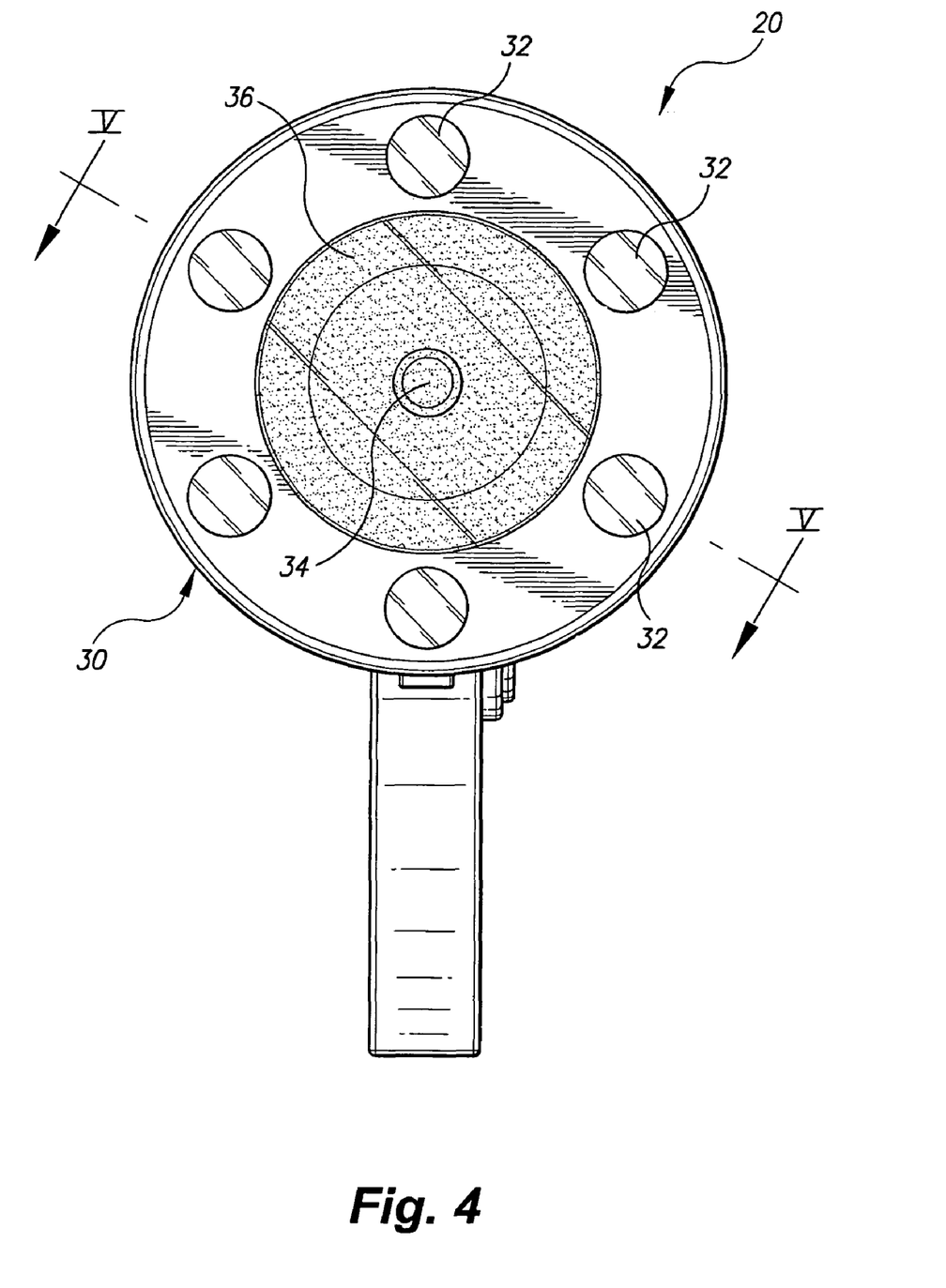
FIG. 4 is a front view of the basic embodiment.
Figure 5:
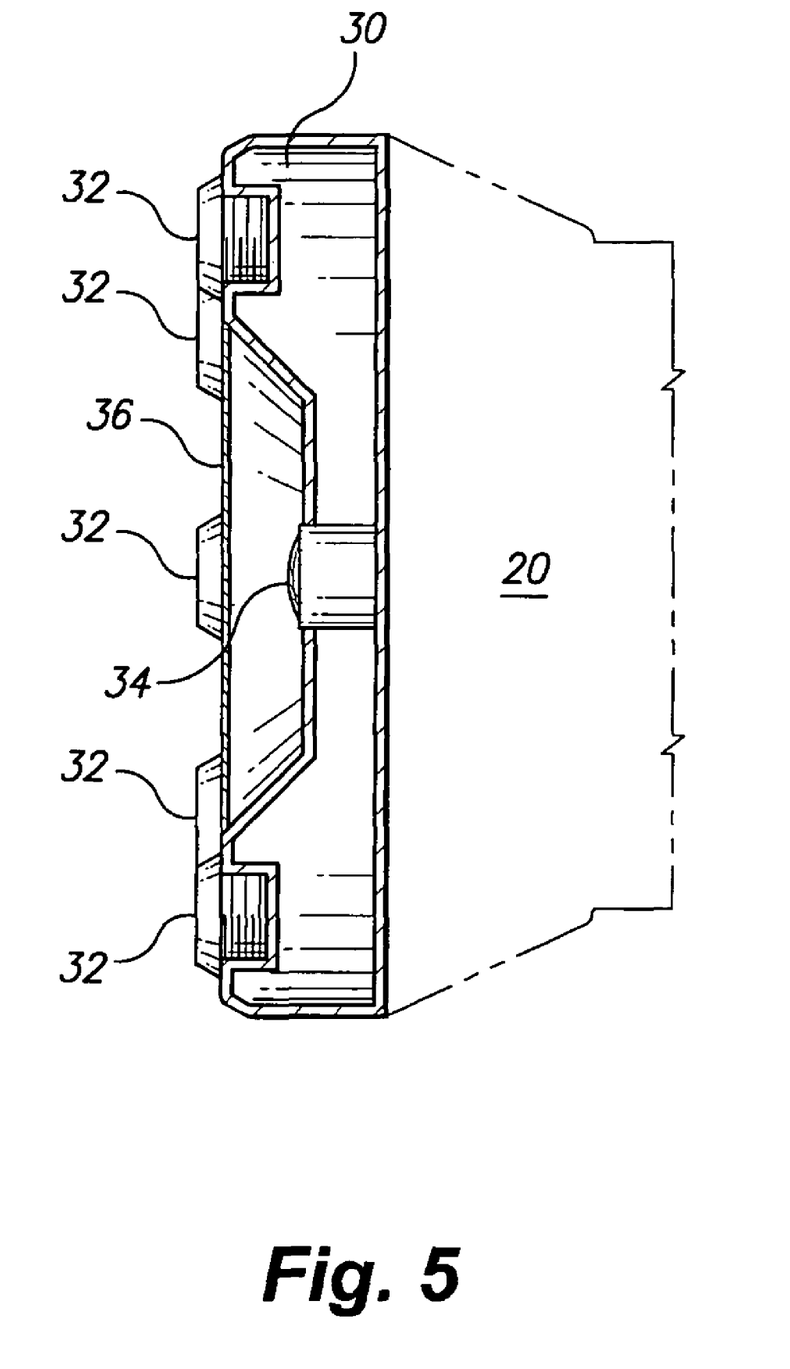
FIG. 5 is a partial sectional view of the basic embodiment shown in FIG. 4 as viewed along section line V shown in FIG. 4.

FIGS. 3, 4, and 5 show the configuration of the most basic embodiment of the inspection tool 20 sensing head 30. FIG. 5 is a partial sectional view of the embodiment shown in FIG. 4 as viewed along section line V shown in FIG. 4. The most basic embodiment of the inspection tool 20 comprises a sensing head 30 that includes a plurality of selectively activated Light Emitting Diodes (LEDs) 32 that project a specific wave band of excitation light on a target area and thereby enhances the on-site inspector's O visual inspection. The wavelength of the projected excitation light is selected so that the light induces fluorescence in a pre-selected type of contamination. The fluorescent light emitted by the contamination passes through a spectral band-pass video camera filter 36 and is detected and recorded by a low-light sensitive video camera 34.

Specifically, the light wavelength band of the fluorescent light emitted by the targeted contamination "corresponds with" (i.e. generally defines) the wavelength band of the light that the spectral band pass filter 36 allows to pass through the filter 36. The fluorescent light passing through the camera filter 36 is detected and recorded by the low-light video camera 34. In other words, the video camera filter 36 is specifically structured so that the pre-selected relatively narrow waveband of light emitted by the fluorescing contamination passes through the filter 36. The video camera 34 enhances the image of the fluorescing contamination and transmits the image to a display (see FIGS. 1, 2, and 11).

In the preferred embodiment, the low-light sensitive camera 34 is a charged coupled device (CCD) digital camera, although an analog camera may also be used. In alternative embodiments, any low-light sensitive camera capable of performing the functions described herein may be used.

In the basic application, the inspection tool 20 is used to detect the presence of a selected type of contamination (e.g. a biofilm) on food processing equipment surfaces. The LEDs 32 project a blue narrow wave band excitation light in the 400 nm to 450 nm spectral band. The projection of the excitation light results in the florescence of the biofilm. Specifically, the biofilm subjected to the excitation light emits florescence in the 600 nm to 650 nm range. The emitted light is detected by the filtered low-light sensitive camera 34 and enhanced and subsequently displayed so that an on-site inspector is alerted to the presence of the biofilm.

In this invention disclosure, the term "contamination" means any biological or non-biological substance of interest that may be detected through the use of the present invention. This includes substances that may be detectable by using adjuvants (such as sprays or liquids) and fluorescent markers that enhance the visualization of a targeted substance. Examples of contaminants include dirt, fecal matter biofilms, chemical residues (including soap or disinfectant residue), and any appropriate organic matter that could support bacterial growth (including blood). Although the example cited supra discloses an excitation light wavelength of 400-450 nm and a camera filter range of 600-650 nm, other ranges should be considered within the scope of the invention. For example, the projection of the excitation light may range from 320 nm to 600 nm and the camera filter may allow light in the 400 nm to 750 nm to pass through to the video camera lens.

Figure 6:
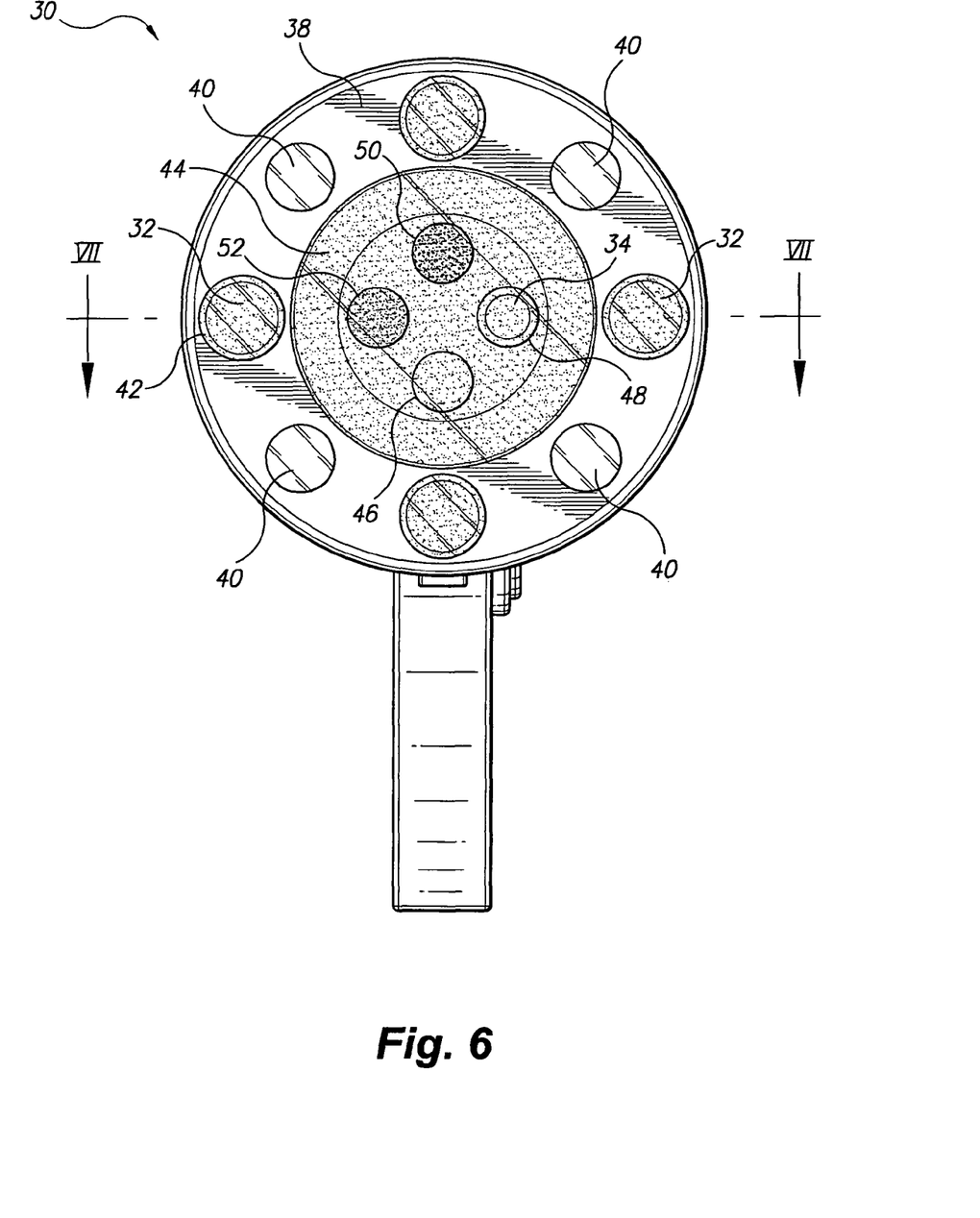
FIG. 6 is a front view of the preferred embodiment.
Figure 7:
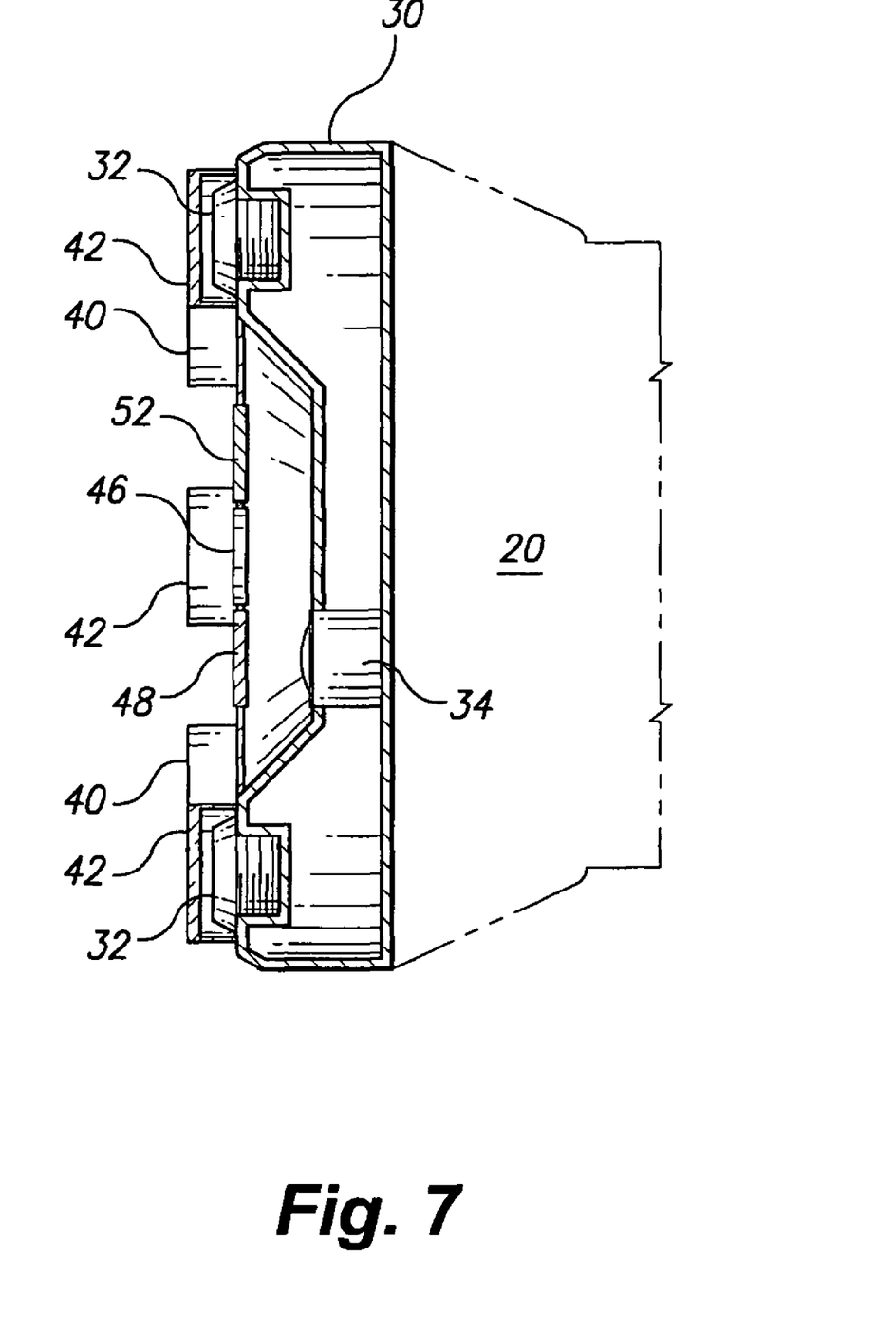
FIG. 7 is a partial sectional view of the preferred embodiment shown in FIG. 6 as viewed along section line VII shown in FIG. 6.

FIGS. 6 and 7 show a front view and a partial sectional side view of the preferred embodiment. Specifically, FIG. 7 is a partial sectional view of the embodiment shown in FIG. 6 as viewed along section line VII shown in FIG. 6. In the preferred embodiment, the sensing head 30 includes a rotatable light filter ring or 38 that is disposed on the outer periphery of the sensing head 30. The rotatable light filter ring 38 comprises at least two types of light filters 40, 42 that may be positioned over a light source 32 such as an LED. The combination of the LED light source 32 and the selectable filters 40, 42 allows an on-site inspector to more specifically select and control the wave length of the excitation light.

FIGS. 6 and 7 show the selection of the light filter associated with reference 42, however, the filter associated with reference number 40 could have been selected by rotating the filter ring 38 either clockwise or counter clockwise. (Note that for the sake of simplicity, in FIG. 6, reference numbers are only shown for selected exemplary filters 40, 42 and lights 32.)

The rotating mechanism associated with the filter ring 38 may include any rotating or dialing mechanism known in the art. Although FIGS. 6 and 7 only show one selected filter 42 and one alternate filter 40, further embodiments may include additional alternate light filters. Although FIGS. 6 and 7 show the light filters arranged in a circular ring, the filters may be arranged in a matrix of any shape. Further, the light source may include non-LED lights and lights of different wavelengths selected to achieve a desired light projection result. In further alternative embodiments, the tool 20 may include a bank of LED lights with different emission wavelengths. Various LEDs or combinations of LEDs may be activated to achieve a desired wavelength emission and intensity.

The preferred embodiment also includes a rotatable camera filter ring 44 so that an on-site inspector can more accurately control the detection and enhancement of any fluorescence emitted by contamination on a specific target object or in a selected area. The rotatable camera filter ring 44 includes a plurality of selectable filters. For example, the embodiment shown in FIG. 6 includes four selectable filters 46, 48, 50, 52. Each of the filters 46, 48, 50, 52 may be rotated to cover the low-light sensitive camera 34. The combination of the selectable light filters 40, 42 and the selectable camera filters 46, 48, 50, 52 allows an on-site inspector to detect and narrowly categorize the identity of specific contamination based on the contamination's fluorescent response to the selected excitation light.

As with the lights and light filters generally described supra, in alternative embodiments, the camera filters may be arranged in various configurations to achieve a desired result. For example, the camera filters may be arranged in a circular ring, or they may be configured in a matrix of any shape. Further, individual camera filters may be combined or modified to achieve a desired filtering result. Although FIGS. 6 and 7 show a rotatable means of moving and selecting alternative light and camera filters, in further embodiments, the light and camera filters may slide linearly or be completely removable and re-attachable. Essentially, any means of changing or substituting alternative light and camera filters should be considered within the scope of the invention.

Figure 8:
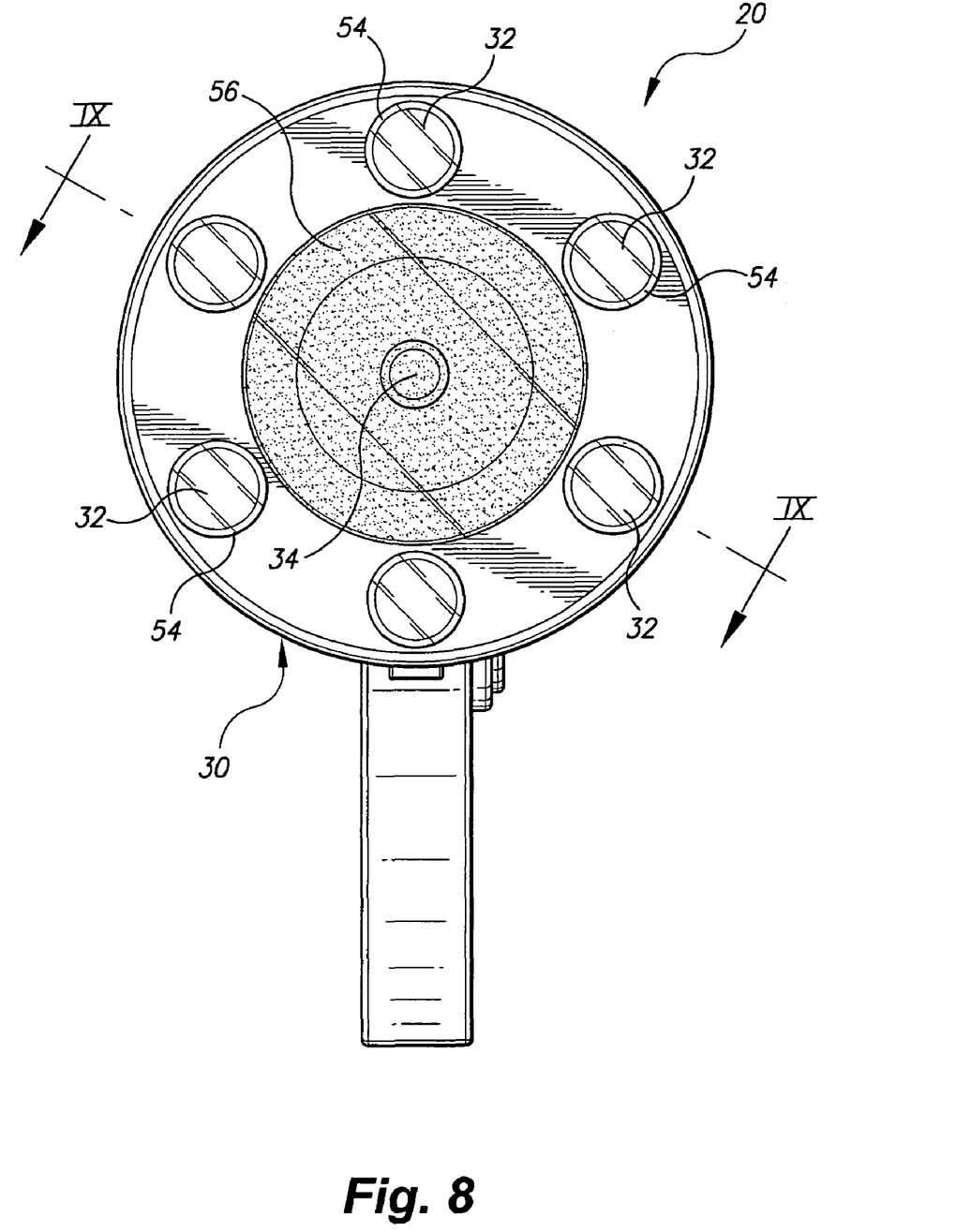
FIG. 8 is a front view of an alternative embodiment of the invention.
Figure 9:
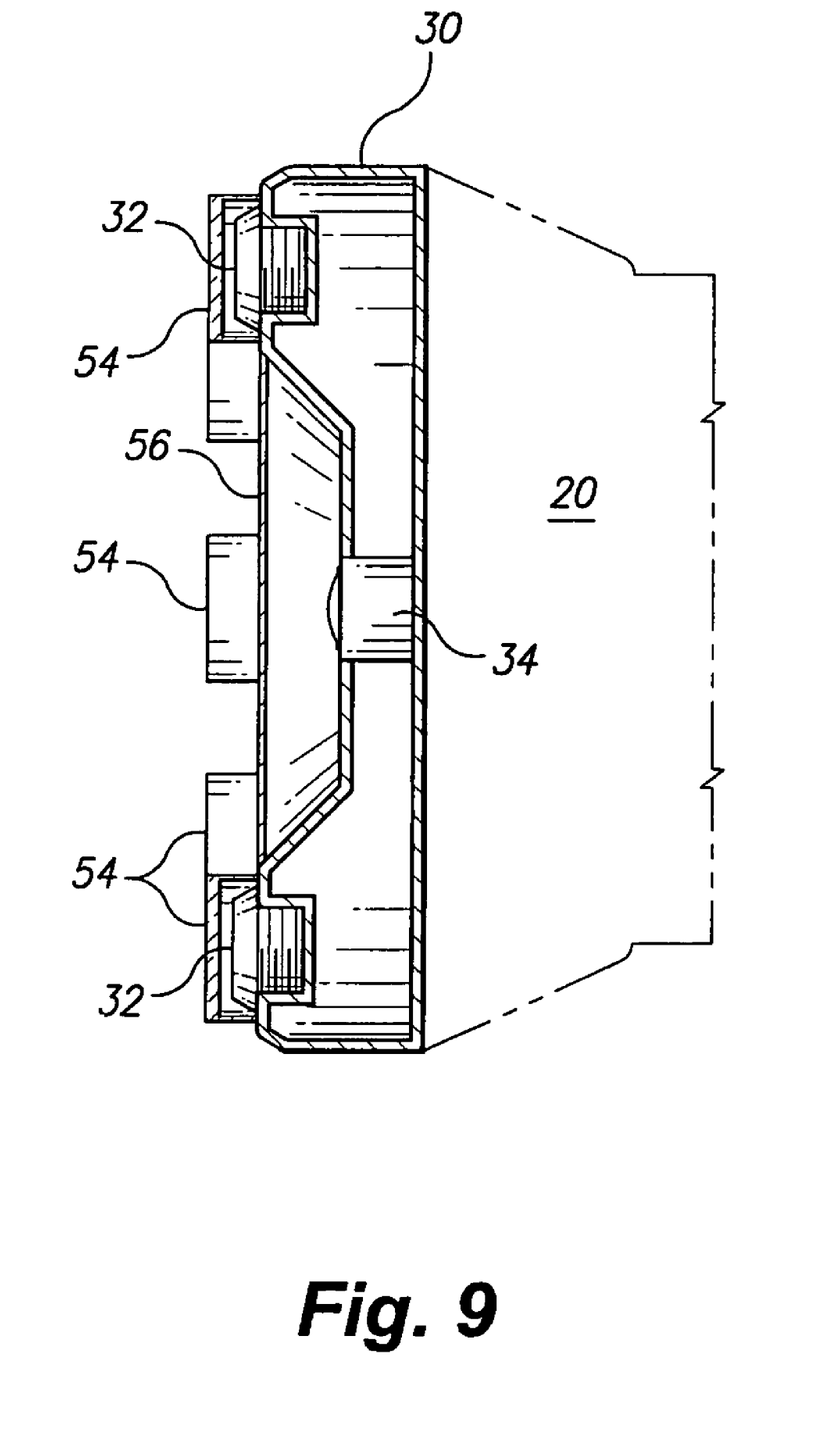
FIG. 9 is a partial sectional view of the alternative embodiment shown in FIG. 8 as viewed along section line IX shown in FIG. 8.

FIGS. 8 and 9 show a further alternative embodiment. FIG. 9 is a partial sectional view of the embodiment shown in FIG. 8 as viewed along section line IX shown in FIG. 8. This embodiment is essentially similar to the basic embodiment shown in FIGS. 3, 4, and 5, however the sensing head 30 of the FIGS. 8 and 9 embodiment includes an electronically tunable light filter 54 disposed over each of the respective LED lights 32, and an electronically tunable camera filter 56 disposed over the low light-sensitive camera 34.

Electronically tunable camera filters 56 and electronically tunable light filters 54 are well known in the art and provide the user with even greater flexibility. Specifically, an electronically tunable light filter 54 allows an on-site inspector to electronically specify the specific wavelengths of the projected light, and an electronically tunable camera filter 56 allows an on-site inspector to electronically specify the wavelengths of light passing through the camera filter 56 and reaching the lens of the low-light camera 34. However, the incorporation of electronic filters significantly increases the production cost of the inspection tool 20 and may render the tool 20 impractical for some users.

Figure 10:
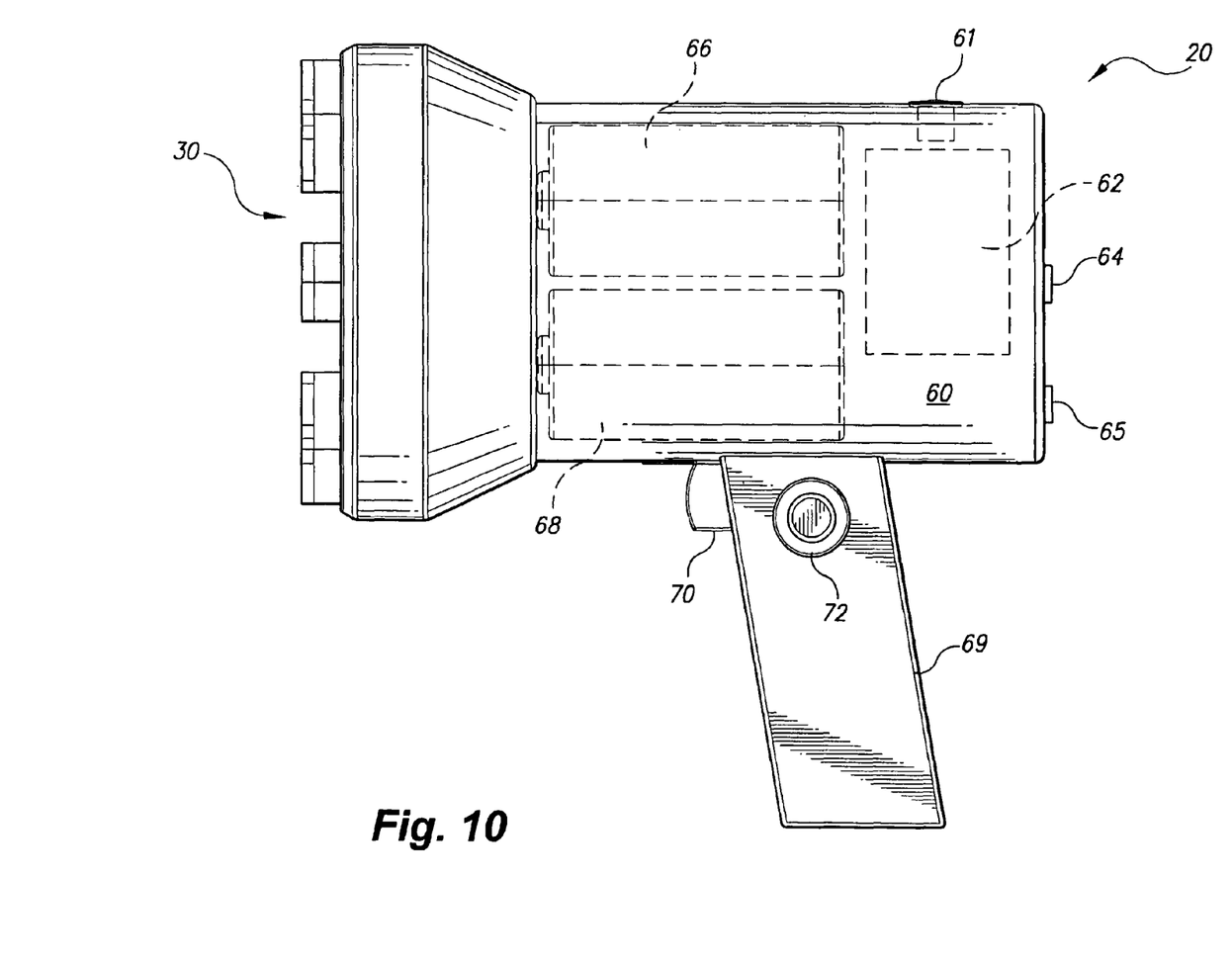
FIG. 10 is a side view of the inspection tool with key interior components shown as dashed lines.

FIG. 10 shows a side view of the inspection tool body 60 with key interior components shown as dashed lines. Specifically, the body 60 of the inspection tool 20 includes a microphone 61 to enable an on-site inspector to narrate an inspection so that the on-site inspector's comments are recorded and/or transmitted. The audio commentary and the video are transmitted to a video and audio sound processor 62. The video and audio sound processor 62 also receives video and audio signals from a wireless processor 66 further discussed infra.

Figure 11:
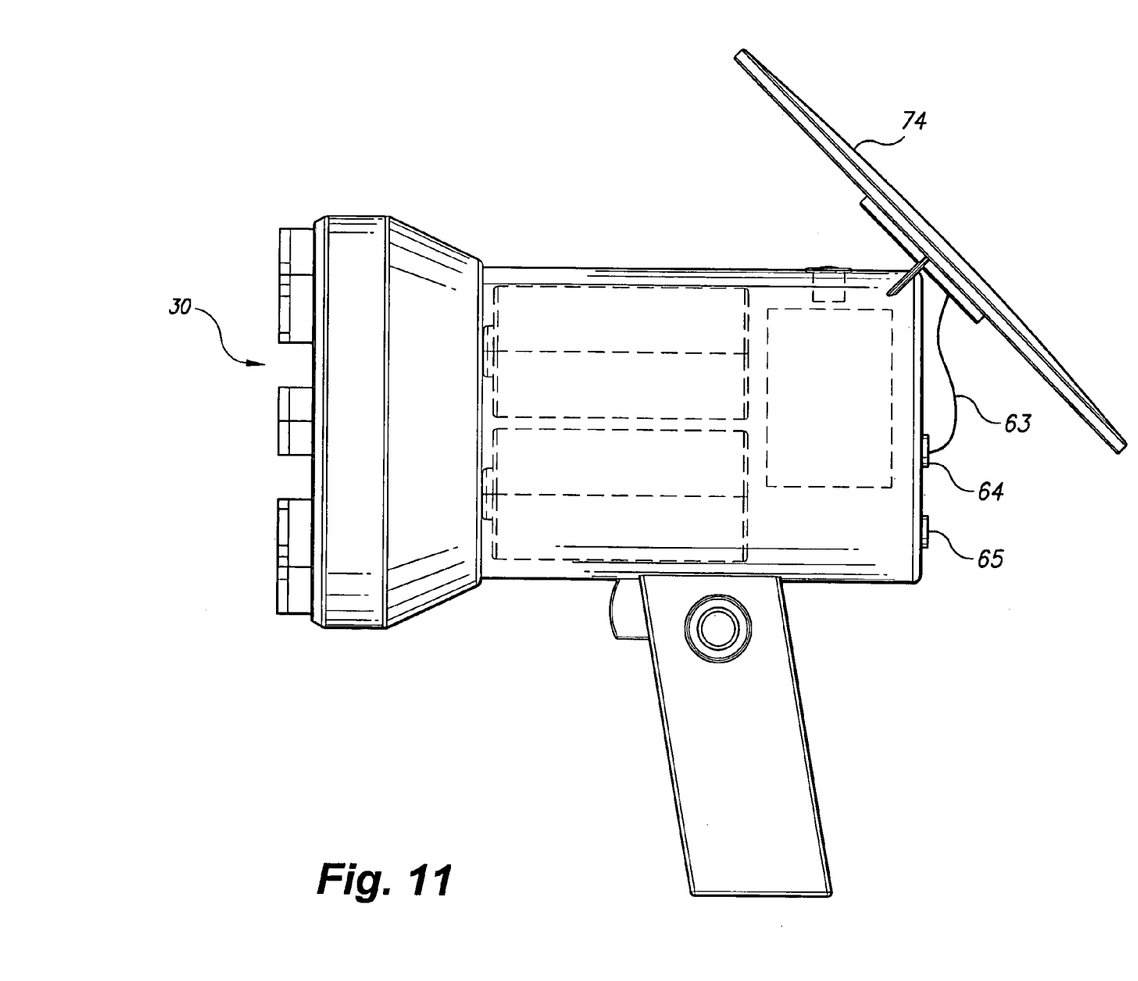
FIG. 11 is a side view of an alternative embodiment of the inspection tool which includes a video display unit.

A video connection jack 64 may be disposed on the inspection tool body 60 to provide a means for connecting various visual displays such as a monocle display system 28 (see FIG. 1), or another type of auxiliary visual display (for example, see FIG. 11). In a further alternative embodiment, a video display may be incorporated directly into the body 60 of the inspection tool 20.

An audio jack 65 allows an on-site inspector to connect the inspection tool 20 to a speaker system 25 (such as headphones, see FIG. 1) so that the inspector can hear audio transmissions from remotely located personnel. Additional input jacks to accommodate various accessories (such as a temperature probe, a barometer, an electronic measuring caliper, a digital weight scale, a bar code reader, a radio frequency identification (RFID) tag/chip detector or reader, etc.) may also be added so that the accessories can communicate with the tool and provide input to the process.

Processed video and audio signals are communicated to and from a wireless processor 66 in the body 60 of the inspection tool 20. The wireless processor 66 transmits data to, and receives data from, electronic equipment exterior to the tool 20. The wireless processor 66 allows the results of an inspection to be transmitted and recorded in real-time as the inspection is on-going, and further enables the reception of audio signals as remotely located personnel interact with the on-site inspector. This capability allows remotely located inspectors to receive the incoming data, conduct a specialized analysis of the data, and transmit the results back to the on-site inspector in real time to further guide the on-site inspector's examination.

In alternative embodiments, an antenna may be added to the tool 20 to further enhance the transmission and reception of wireless data. In addition to the wireless transmission means, data from the tool 20 may also be communicated to and from the tool 60 via a standard hard-wired cable connection or a similar non-wireless means.

As shown in FIG. 10, the tool 20 may be powered by an electrical power supply module such as a battery 68. The tool 20 may also be configured so that it is simply plugged into a wall socket or otherwise powered by an auxiliary means. In further alternative embodiments, the tool 20 may be powered by any means known in the art.

Although the basic functions of the audio/video processor 62 and the wireless transmitter 66 are generally discussed supra, the specific configuration of the components may include any combination of receiving, processing and transmitting elements known in the art, consistent with the functions described. Any combination of digital and analog processing and transmission components should be considered within the scope of the invention, including exclusively digital and exclusively analog means.

As shown in FIG. 10, the tool hand grip 69 supports the tool body 60 during normal inspection operations. The hand grip 69 includes a selective LED activation switch 70 so that the LED lights are only activated when needed. This may be particularly important when operating on battery power. A selective video/sound transmission switch 72 is also disposed on the hand grip 69 so that an on-site inspector can stop and start the transmission of data during an inspection. A locking mechanism built into these switches 70, 72 may lock either one of these switches in the "on" position, as required.

An alternative video display unit 74 is shown in FIG. 11. The alternative video display unit 74 is comprised of a standard computer video display screen that is well known in the art. The tool 20 communicates with the video display unit 74 via a cable 63 connected to the video connection jack 64. The length of the cable 63 may optionally be increased so that the tool 20 may be moved into hard-to-reach locations while the video display unit 74 remains accessible. In further alternative embodiments, the tool 20 may communicate with the display unit 74 wirelessly or the tool 20 may be attached to a larger fixed video monitor via a lengthened cable 63. In further embodiments, a single tool 20 may accommodate more than one display unit 74.

The video display unit 74 is larger than the monocle display system 28 (see in FIG. 1) and enables more than one on-site inspector to view the enhanced display. The video display unit 74 may be used alone or in combination with the monocle display system 28. In the most basic application, the inspection tool 20 may not include a transmitting and/or recording capability so that the results of the inspection are only visible to the operating inspector.

In addition to the images acquired by the inspection tool 20 low-light camera 34, a variety of associated data may also be gathered and used to supplement the camera images. For example, the associated data may include at least the following information: 1) a time/date stamp to document and communicate the time and date of the inspection; 2) global positioning system (GPS) coordinates to document and communicate the location of the inspection; 3) on-site inspector information identifying the specific inspector; 4) environmental information such as ambient temperature and humidity, etc; 5) readings from accessory equipment such as a temperature probe or digital weight scale, etc.; 6) any other data deemed relevant to the inspection. To ensure the accuracy of the information, the data could be certified through trusted independent organizations by methods such as specialized calibration, tamper-proof instruments, or specialized monitoring and the like.

Figure 12:
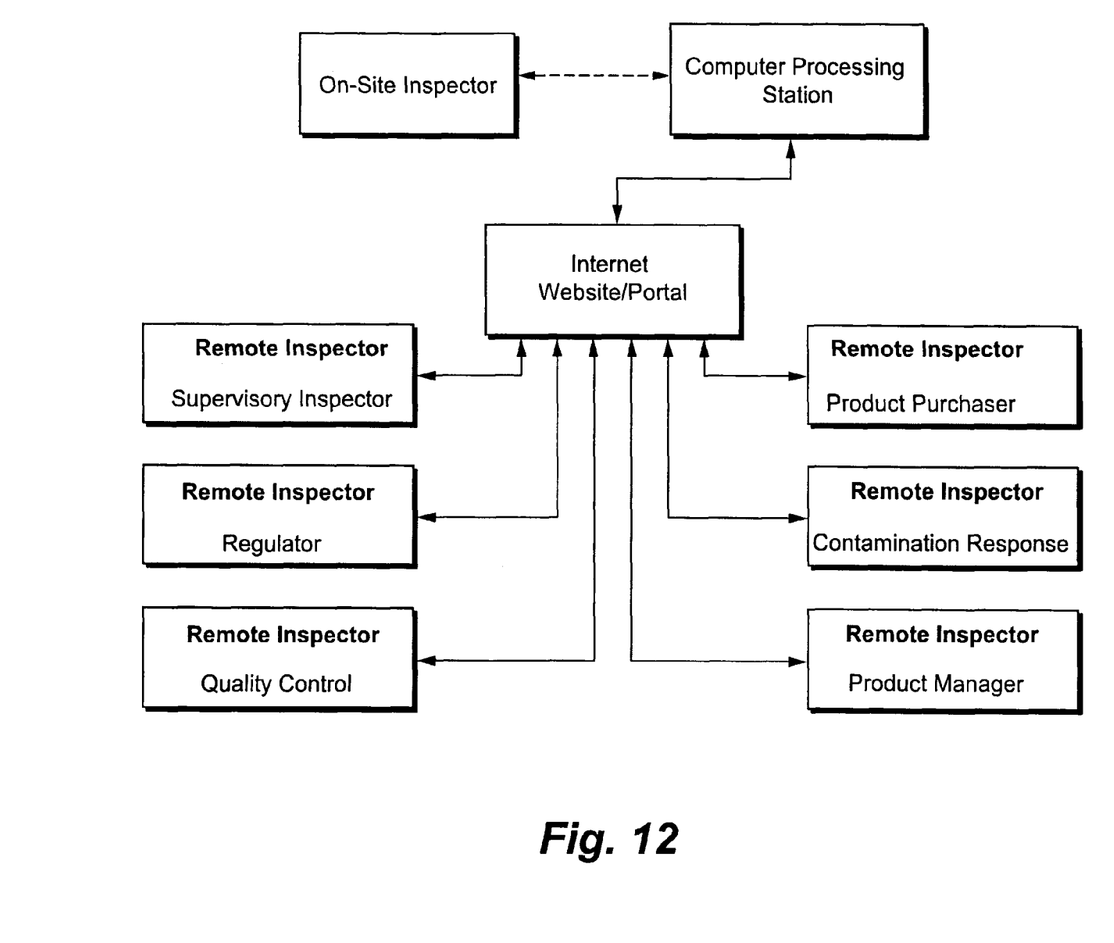
FIG. 12 is a flow chart of the inspection data transmission process.

FIG. 12 schematically shows the data transmission process of the preferred embodiment of the current invention. After the data and images are acquired, they may be transmitted wirelessly to a computer processing station and then streamed or otherwise uploaded to an internet web site or other information portal. In the preferred embodiment, the computer processing station is a laptop computer, but the processing station may also comprise a computer system with significantly greater processing ability, including the ability to access multiple relevant databases and manipulate the audio and video feed to most effectively and efficiently manage and communicate the information.

Wireless transmission of the data may be handled through standardized WiFi protocols and equipment. Standard WiFi protocols are a, b, g, and most recently n. Standardized protocols include data encryption standards that would allow data to be securely transmitted over the Internet. Alternatively the inspection information may be transferred by any means known in the art.

Once the data is available on the internet, the data may be accessed by multiple personnel with significant roles in the inspection and production process. As shown in FIG. 11, these personnel include supervisory personnel, regulators, quality control specialists, potential product purchasers (customers), contamination response teams, and the operational product manager.

Internet (or intranet) availability of the data is particularly valuable because it allows an organization to leverage its inspection expertise by (for example) having a single senior inspector at a fixed site oversee inspections by less experienced on-site inspectors at multiple sites. Given the ability of a remotely located senior inspector to direct the inspection, it may no longer be necessary for the on-site personnel to be qualified inspectors.

The real-time transmission of audio and video data enables an organization to have a "second set of eyes" to oversee inspections without the necessity of having a second inspector also at the site of the inspection. The ability to have the input of a more experienced inspector is particularly valuable when on-site real-time decisions must be made, such as the decision to investigate a problem further or stop (or not stop) production. This ability alone may save significant amounts of money and/or prevent future food-related illnesses and possibly deaths.

The current invention includes the capability for the remotely located personnel to interactively manipulate the data acquired by the on-site inspector and communicate the results back to the on-site inspector in real time. This interactive process could (for example) significantly improve the efficiency and efficacy of processes like the ATP (Adenosine Triphosphate) swab tests. The ability of remotely located personnel to direct the on-site inspector and perform simultaneous tests could negate the necessity for follow-up inspections and thereby reduce the time and expense of the inspection process.

The data may be viewed by the remotely located inspectors in a variety of ways, including via a split screen format. For example, one side of a remotely located inspector's display screen may show an overhead view of the on-site inspector as he conducts the inspection, and the other half of the screen may display the actual transmission from the inspection tool 20 low-light camera 34. The screen may be split again to show an unenhanced (normally lighted) close-up of the target area/object of the inspection. The screen may be further divided to show other relevant information downloaded from a computer data base. The data base information may include general or historical information regarding the general type of object inspected, or more specific information regarding the individual object or group of objects inspected In general, the data may be displayed in any manner known in the art to facilitate an efficient and rigorous inspection.

For the foregoing reasons, it is clear that the invention provides an innovative compact inspection tool that may be used in multiple inspection applications. Although the primary application of the tool is in the inspection of items related to food processing, the invention also has application in multiple other fields that require clean facilities, such as clean rooms related to surgery and other medical treatments, the manufacture of pharmaceuticals, the manufacture of equipment related to information technologies (computer chips, photography, etc.), and the like. The invention may also have application in the context of various types of investigations such as crime scene investigations, accident investigations, tampering, and generally any type of process in which the discovery of contamination comprises significant information.

The invention may be modified in multiple ways and applied in various technological areas. For example, the sensing head may be specially shaped to access hard-to-reach areas that would not otherwise be apparent.

Although the materials of construction are not described, they may include a variety of compositions consistent with the function of the invention. For example, although the outer components are generally assumed to be plastic, they may also be comprised of metals or composite materials to enhance the durability of the tool. Such variations are not to be regarded as a departure from the spirit and scope of the invention, and all such modifications as would be obvious to one skilled in the art are intended to be included within the scope of the following claims.

What is claimed is:

1. A hand-held inspection tool, the tool comprising:
   a tool body,
   a sensing head connected to the tool body, the sensing head comprising:

(a) a video camera;
(b) a video camera lens fitted on the video camera and exposed on a face of the sensing head;
(c) a spectral band pass video camera filter matrix comprising at least two video camera filters, the video camera filter matrix being configured so that each of the at least two video camera filters can selectively be positioned to cover the video camera lens, each of the video camera filters being structured to allow only a selected wave band of light to pass through the video camera filter to the video camera lens; and,
(d) at least one excitation light disposed on the face of the sensing head, the at a video processor receiving and transmitting the video images from the video camera;
a visual display receiving and displaying the images from the video processor; and,
a hand grip for supporting the tool body and the sensing head;
wherein an operator moves the inspection tool via the hand grip to the target contamination and directs the at least one light so that the fluorescence emitted by the target contamination is detected and transmitted by the video camera and shown on the visual display.

2. The inspection tool as described in claim 1 wherein the video processor comprises a means of recording and transmitting audio signals corresponding with the detected and transmitted video signals.

3. The inspection tool as described in claim 2 wherein the video processor further comprises a wireless transmitting means for wirelessly transmitting the recorded audio and the recorded video to a computer processing station.

4. The inspection tool as described in claim 3 further comprising an uploading means for uploading the recorded audio and video to a computer-accessible information portal.

5. The inspection tool as described in claim 4 wherein the computer-accessible information portal is an internet web site.

6. The inspection tool as described in claim 5 further comprising a distribution means for distributing the audio and video to remotely located inspectors.

7. The inspection tool as described in claim 6 further comprising a receiving means for receiving audio and video from remotely located inspectors, the receiving means communicating the audio and video to the tool.

8. The inspection tool of claim 1 wherein the sensing head is attached to a first end of the inspection tool body, and the hand grip extends normal to the tool body.

9. The inspection tool of claim 1 wherein the video camera is a low-light sensitive camera.

10. The inspection tool of claim 9 wherein the video camera is a digital camera.

11. The inspection tool of claim 10 wherein the video camera is a charged coupled device (CCD) camera.

12. The inspection tool of claim 1 wherein the multiple video camera filters are disposed in a rotatable camera filter ring so that individual video camera filters selectably cover the video camera lens.

13. The inspection tool of claim 1 wherein the video camera filter is an electronically tunable filter.

14. The inspection tool of claim 1 wherein the at least one light is comprised of multiple lights disposed on the sensing head, one or more of the lights being selectively activated by the operator.

15. The inspection tool of claim 14 wherein each of the multiple lights are light emitting diodes (LEDs).

16. The inspection tool of claim 15 wherein a light filter covers each of the respective LEDs.

17. The inspection tool of claim 14 wherein the multiple lights are covered by a rotatable light filter ring disposed on the sensing head so that a light filter covers each one of the respective multiple lights.

18. The inspection tool of claim 17 wherein the rotatable light filter ring is structured so that an alternate light filter is selectable by rotating the light filter ring.

19. The inspection tool of claim 1 wherein the hand grip includes a trigger switch activating the at least one light.

20. The inspection tool of claim 1 wherein the trigger switch is lockable in the "on" position.

21. The inspection tool of claim 1 wherein the hand grip includes a data transmission switch.

22. The inspection tool of claim 1 wherein the data transmission switch is lockable in the "on" position.

23. The inspection tool of claim 1 wherein the at least one light is structured to project light in the 320 nm to 600 nm spectral band, and the at least one video camera filter is structured to allow light in the 400 nm to 750 nm spectral band to pass through the video camera filter and into the video camera lens of the video camera.

24. The inspection tool of claim 1 wherein the inspection tool is powered by a battery.

25. The inspection tool of claim 1 wherein the inspection tool is powered by an AC power source.

26. A hand-held inspection tool, the tool comprising:
a tool body,
a sensing head connected to the tool body, the sensing head comprising:
(a) a video camera disposed in the sensing head, the video camera recording detected video images;
(b) a video camera lens fitted on the video camera and disposed on a face of the sensing head;
(c) a spectral band pass video camera filter matrix comprising at least two video camera filters, the video camera filter matrix being configured so that each of the at least two video camera filters can selectively be positioned to cover the video camera lens, each of the video camera filters being structured to allow only a selected wave band of light to pass through the video camera filter to the video camera lens;
(d) at least one excitation light disposed on the face of the sensing head, and
(e) at least two light filters, at least one of the at least two light filters covering the at least one light, each of the at least two light filters being structured to induce target contamination to emit fluorescence corresponding with the wave band of light that passes through the video camera filter selectively positioned over the video camera lens;
a video processor receiving and transmitting the video images from the video camera;
a visual display receiving and displaying the images from the video processor; and,
a hand grip for supporting the tool body and the sensing head;
wherein an operator moves the inspection tool via the hand grip to the target contamination and directs the at least one light so that the fluorescence emitted by the target contamination is recorded by the video camera and shown on the visual display.

27. A method of conducting an inspection comprising the steps of:
providing a hand-held inspection tool body;
attaching a sensing head to the tool body;

installing a video camera into the sensing head so that the lens of the video camera is exposed on a face of the sensing head;

covering the lens of the video camera with a spectral band-pass video camera filter so that only a selected wave band of light passes through the video camera filter to the video camera lens;

positioning at least one excitation light on the face of the sensing head so that the at least one light induces target contamination to emit fluorescence corresponding with the selected wave band of light that passes through the video camera filter to the video camera lens;

providing a processor in the tool to receive and transmit video images from the video camera;

attaching a display to the tool to view the video images transmitted from the processor;

supporting the tool body and sensing head with a hand grip attached to the tool body;

activating the at least one light and directing the sensing head toward an area of interest so that any of the target contamination in the area of interest emits fluorescence, the fluorescence being detected by the video camera and being displayed on the display to alert a tool operator to a presence of the target contamination.

28. The method of claim 27 further comprising the step of enabling the processor to wirelessly transmit video and audio information to a computer processing station.

29. The method of claim 28 further comprising the step of uploading the transmitted video and audio information to a computer-accessible information portal.

30. The method of claim 29 wherein the computer-accessible information portal is an internet site.

31. The method of claim 30 wherein a computer-accessible information portal is an intranet.

32. The method of claim 31 wherein, after the providing step, stamping the transmitted video with a time stamp.

33. The method of claim 32 wherein the time stamp is certified by an independent source.

34. The method of claim 33 wherein, after the enabling step, further enabling the video processor to receive audio and video information from remotely located inspectors through the computer processing station.

* * * * *

UNITED STATES PATENT AND TRADEMARK OFFICE
CERTIFICATE OF CORRECTION

PATENT NO.         : 8,310,544 B2  
APPLICATION NO.    : 12/157911  
DATED              : November 13, 2012  
INVENTOR(S)        : Moon S. Kim et al.

It is certified that error appears in the above-identified patent and that said Letters Patent is hereby corrected as shown below:

In the Claims

In column 9, lines 12-14 should read (d) at least one excitation light disposed on the face of the sensing head, a video processor receiving and transmitting the video images from the video camera;

Signed and Sealed this  
Fifteenth Day of December, 2015

Michelle K. Lee  
*Director of the United States Patent and Trademark Office*